(12) United States Patent
Muccio

(10) Patent No.: US 11,857,395 B2
(45) Date of Patent: Jan. 2, 2024

(54) TRIPLE FLEXION DEVICE

(71) Applicant: Philip Muccio, Ypsilanti, MI (US)

(72) Inventor: Philip Muccio, Ypsilanti, MI (US)

( * ) Notice: Subject to any disclaimer, the term of this patent is extended or adjusted under 35 U.S.C. 154(b) by 333 days.

(21) Appl. No.: 15/316,039

(22) PCT Filed: Jun. 4, 2015

(86) PCT No.: PCT/US2015/034214
§ 371 (c)(1),
(2) Date: Dec. 2, 2016

(87) PCT Pub. No.: WO2015/187961
PCT Pub. Date: Dec. 10, 2015

(65) Prior Publication Data
US 2017/0105864 A1    Apr. 20, 2017

Related U.S. Application Data

(60) Provisional application No. 62/007,729, filed on Jun. 4, 2014.

(51) Int. Cl.
*A61F 5/01*     (2006.01)

(52) U.S. Cl.
CPC .......... *A61F 5/0113* (2013.01); *A61F 5/0102* (2013.01); *A61F 5/0106* (2013.01)

(58) Field of Classification Search
CPC .... A61F 5/0113; A61F 5/0116; A63B 21/143; A63B 21/1449; A63B 23/085; A63B 23/08
See application file for complete search history.

(56) References Cited

U.S. PATENT DOCUMENTS

| 1,548,711 | A | * | 8/1925 | Cooper | A61F 5/0104 |
| | | | | | 602/25 |
| 4,252,112 | A | * | 2/1981 | Joyce | A61F 5/0104 |
| | | | | | 602/26 |
| 6,428,495 | B1 | * | 8/2002 | Lynott | A61F 5/3715 |
| | | | | | 602/23 |
| 2004/0199095 | A1 | * | 10/2004 | Frangi | A63B 71/1225 |
| | | | | | 602/26 |
| 2015/0119781 | A1 | * | 4/2015 | Ponce | A61H 1/0237 |
| | | | | | 602/28 |

\* cited by examiner

*Primary Examiner* — Tarla R Patel
(74) *Attorney, Agent, or Firm* — Mindful IP PLLC; Michael J. McCandlish

(57) ABSTRACT

A device promotes triple flexion of the hip, knee and ankle. The device includes a belt, knee cuff, ankle wrap, foot wrap and two pairs of adjustable bands. The device is configured to promote triple flexion in the hip, knee and ankle of the user during the swing phase of walking when the user has the belt wrapped around the user's waist, the knee cuff wrapped around the user's knee, the ankle wrap wrapped around the user's ankle and the foot wrap wrapped around the user's foot.

7 Claims, 10 Drawing Sheets

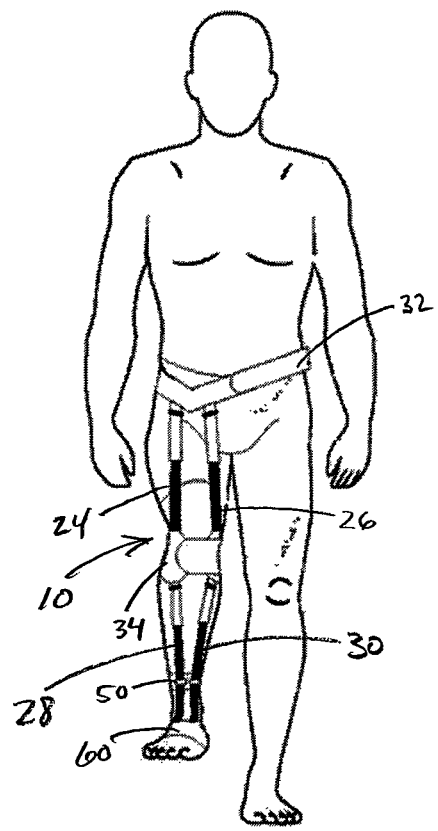
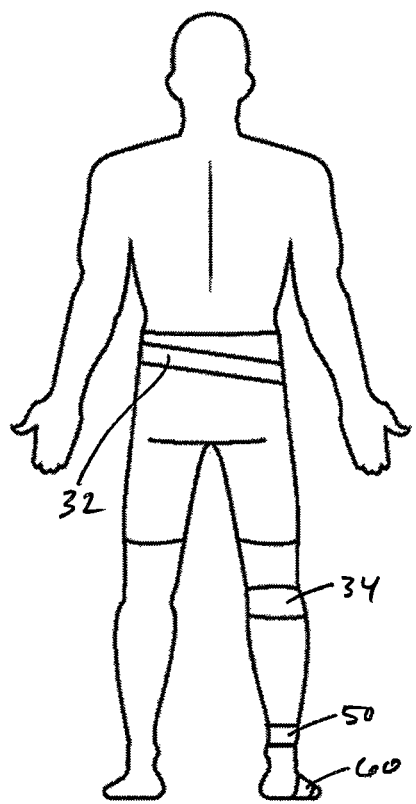
Fig. 6                Fig. 7
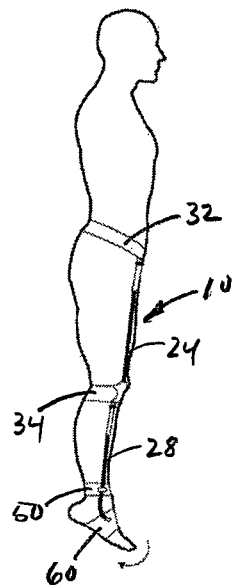
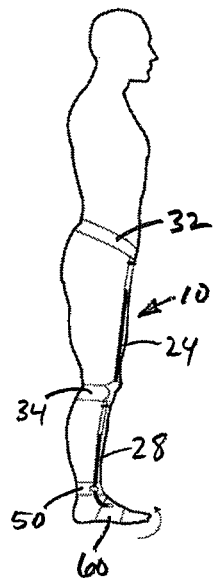
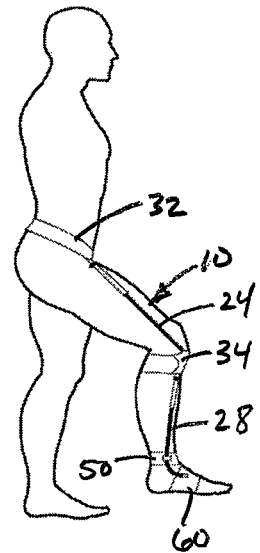
Fig. 8        Fig. 9        Fig. 10

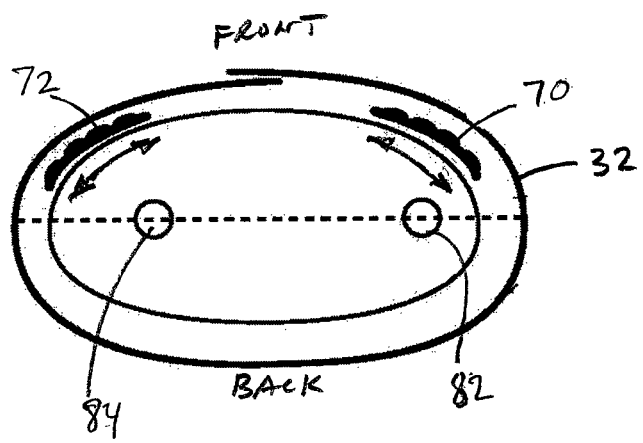
Fig. 24
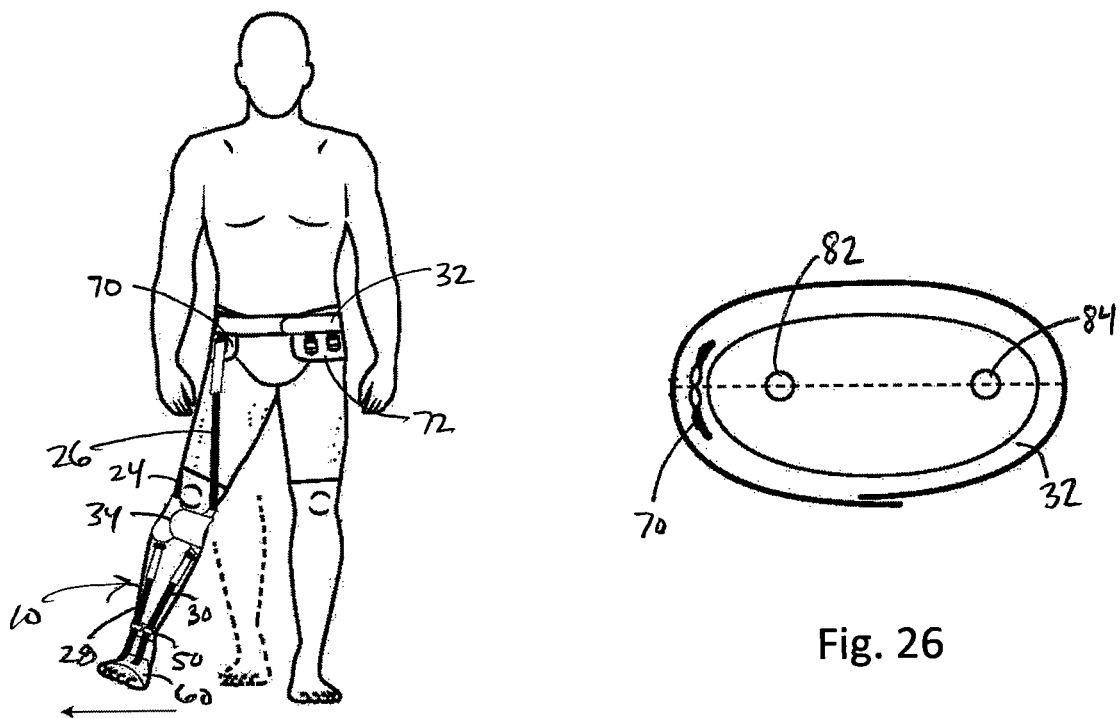
Fig. 26
Fig. 25

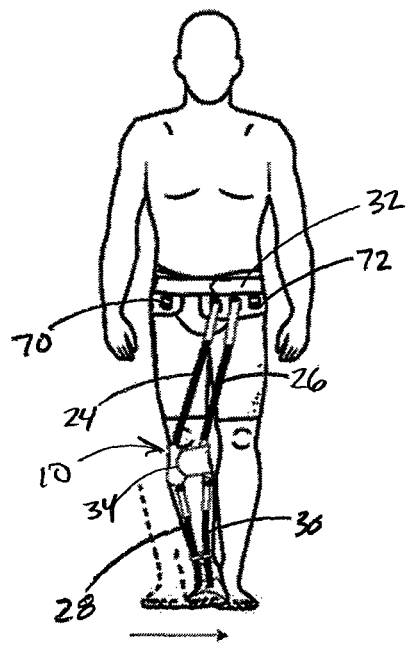
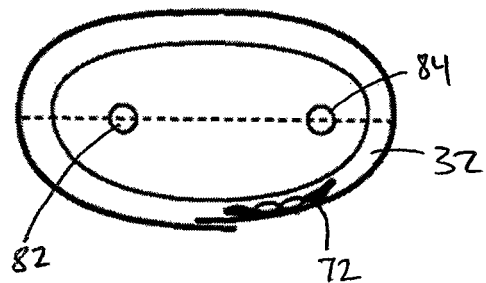
Fig. 27
Fig. 28
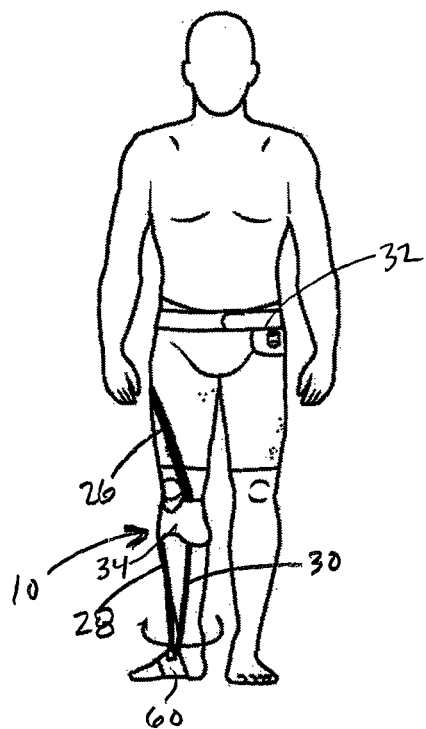
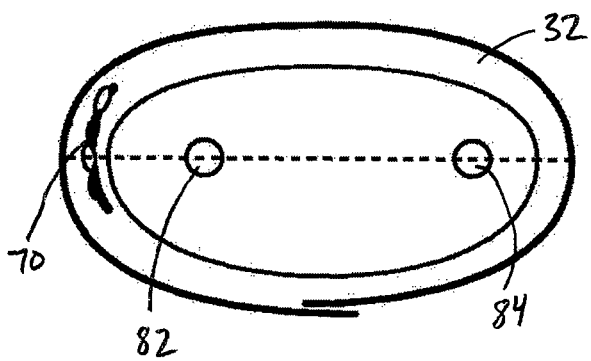
Fig. 29
Fig. 30

TRIPLE FLEXION DEVICE

RELATED APPLICATIONS

This application claims the benefit of U.S. Provisional Patent Application No. 62/007,729, filed on Jun. 4, 2014. This application is also a national stage filing of PCT/US2015/034214, filed on Jun. 4, 2015. The entire contents of the above applications are incorporated herein by reference.

FIELD

The present invention relates to devices that facilitate or promote flexion of a joint in a human body and, in particular, a wearable device that facilitates the flexion of at least three joints during the swing phase of walking.

BACKGROUND

Paralysis of the lower extremity can result in the loss of hip and knee flexion (hip and knee drop) and ankle flexion (foot drop) during the swing phase of walking. The hip, knee and ankle flex to pick the leg up to clear the ground to prevent dragging of the foot or tripping. The muscles responsible for this activity can become paralyzed through injury, disease or non-use (disuse muscle atrophy) that results in the inability to pick the leg up when walking.

Triple flexion is the combination of hip 12, knee 14 and ankle flexion 16 that takes place during the swing phase of walking, as shown in FIG. 1. Triple Flexion occurs when the hip flexors 18 (illiopsoas, illiacus), the knee flexors 20 (hamstrings) and the ankle flexors 22 (dorsiflexors) contract in the swing phase of gait, as shown in FIG. 2. Hip, knee and foot drop occur when the muscles responsible for flexing these joints are unable to do so due to paralysis. Paralyzed hip, knee and ankle flexing muscles result in hip, knee and foot drop, as shown in FIG. 3.

There are a number of remedies to correct foot drop in real-time, but there are very few practical options for treating hip and knee drop. Traditional orthotics are designed to stabilize joints or provide some movement and flexibility of the joint through springs and flexible plastics, but these only work well for the foot, not the hip and knee because the weight of the leg is significantly greater than the mechanical torque that can be generated through traditional orthotic joints. Furthermore, traditional orthotics are heavy, restrictive, can cause pressure and skin breakdown and do not fit easily under clothing. While orthotics can control foot drop, they are often heavy, bulky, do not fit well into shoes, require one set of shoes to attach the orthotic to and skin pressure and breakdown is common. The other drawback is that many orthotic devices have to be custom fit. Many patients find the cosmetic aspect of orthotics objectionable and/or dislike the biomechanics produced by them, so they choose to abandon them despite the correction achieved.

Accordingly, there is room in the art for a device to address the needs of a person that has paralysis or injury that is causing hip, knee and foot drop. Moreover, there is need for a device that is not heavy and restrictive that does not create pressure against the skin and cause skin breakdown.

SUMMARY

In an aspect of the present invention, a device for promoting triple flexion of the hip, knee and ankle is provided. The device includes a belt, knee cuff, ankle wrap, foot wrap and two pairs of adjustable bands.

In accordance with an embodiment of the present invention, the device is configured to promote triple flexion in the hip, knee and ankle of the user during the swing phase of walking when the user has the belt wrapped around the user's waist, the knee cuff wrapped around the user's knee, the ankle wrap wrapped around the user's ankle and the foot wrap wrapped around the user's foot.

In accordance with another embodiment of the present invention, the belt is configured to be worn around a waist of a user.

In accordance with another embodiment of the present invention, the belt is V-shaped and configured to be worn around a waist of a user.

In accordance with yet another embodiment of the present invention, the knee cuff configured to wrap around a knee of the user and is positioned below the belt.

In accordance with yet another embodiment of the present invention, the foot wrap is configured to wrap around a foot of the user and is positioned below the knee cuff.

In accordance with yet another embodiment of the present invention, the ankle wrap is configured to wrap around an ankle of the user and positioned between the knee cuff and the foot wrap, wherein the ankle wrap has two loops for receiving there through the second pair of adjustable bands.

In accordance with yet another embodiment of the present invention, the first pair of adjustable bands each have a first end adjustably connected to the belt and a second end securely fixed to the knee cuff and the second pair of adjustable bands each have a first end adjustably connected to the knee cuff and a second end securely fixed to the foot wrap.

In accordance with still another embodiment of the present invention, the belt is fastened to the user's waist using a hook and loop fastener.

In accordance with still another embodiment of the present invention, the belt has a padded underside.

In accordance with still another embodiment of the present invention, the knee cuff has a u-shaped cut out.

In accordance with still another embodiment of the present invention, the knee cuff has a plurality of stiffening members.

In accordance with still another embodiment of the present invention, the knee cuff has a hook and loop fastener to fasten the knee cuff around the user's knee.

In accordance with still another embodiment of the present invention, the ankle wrap has a hook and loop fastener to fasten the ankle wrap around the user's ankle.

In accordance with still another embodiment of the present invention, the foot wrap has a hook and loop fastener to fasten the foot wrap around the user's foot.

Further features, advantages and areas of applicability will become apparent from the description provided herein. It should be understood that the description and specific examples are intended for purposes of illustration only and are not intended to limit the scope of the present disclosure.

DRAWINGS

The drawing described herein is for illustration purposes only and is not intended to limit the scope of the present disclosure in any way. In the drawing:

FIG. 6 is a schematic drawing of a front view of a human being wearing the triple flexion device, in accordance with the principles of the present invention;

FIG. 7 is a schematic drawing of a back view of a human being wearing the triple flexion device, in accordance with the principles of the present invention;

FIG. 8 is a schematic drawing of a side view of a human being wearing the triple flexion device configured to allow the foot to plantarflex, in accordance with the principles of the present invention;

FIG. 9 is a schematic drawing of a side view of a human being wearing the triple flexion device configured to flex the foot and ankle to 90 degrees or to a more acute angle, in accordance with the principles of the present invention;

FIG. 10 is a schematic drawing of a side view of a human being wearing the triple flexion device configured to flex the hip, knee and ankle to lift the leg from the ground, in accordance with the principles of the present invention;

FIG. 24 is a schematic drawing of a cross-section of a human being at the hip centers wearing the triple flexion device and illustrating the locations of the panels on the belt, in accordance with the principles of the present invention;

FIG. 25 is a schematic drawing of a front view of a human being standing and wearing the triple flexion device configured to abduct the hip, in accordance with the principles of the present invention;

FIG. 26 is a schematic drawing of a cross-section of a human being at the hip centers wearing the triple flexion device and illustrating the location of the adjustable panel on the belt to abduct the hip, in accordance with the principles of the present invention;

FIG. 27 is a schematic drawing of a front view of a human being standing and wearing the triple flexion device configured to adduct the hip, in accordance with the principles of the present invention;

FIG. 28 is a schematic drawing of a cross-section of a human being at the hip centers wearing the triple flexion device and illustrating the location of the adjustable panel on the belt to adduct the hip, in accordance with the principles of the present invention;

FIG. 29 is a schematic drawing of a front view of a human being standing and wearing the triple flexion device configured to rotate the right hip, in accordance with the principles of the present invention;

FIG. 30 is a schematic drawing of a cross-section of a human being at the hip centers wearing the triple flexion device and illustrating the location of the adjustable panel on the belt to rotate the right hip, in accordance with the principles of the present invention;

Figure 34:
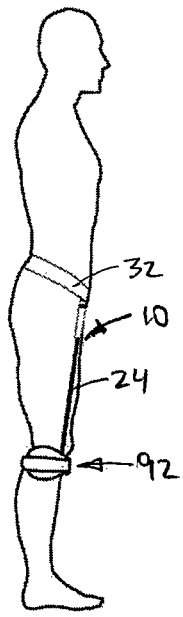
Figure 35:
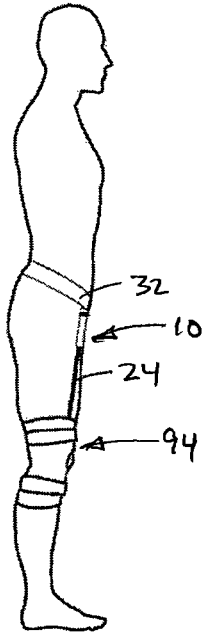

FIG. 34 is a schematic drawing of a side view of a human being wearing the triple flexion device in combination with a Functional Electrical Stimulation device, in accordance with the principles of the present invention; and FIG. 35 is a schematic drawing of a side view of a human being wearing the triple flexion device in combination with a Knee Orthosis, in accordance with the principles of the present invention.

DETAILED DESCRIPTION

The following description is merely exemplary in nature and is not intended to limit the present disclosure, application, or uses.

Figure 1:
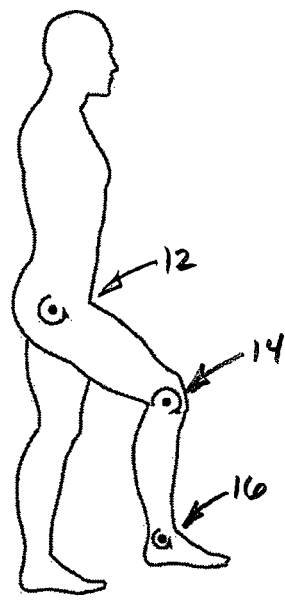
FIG. 1 is a schematic drawing of a human being demonstrating triple flexion which is the combination of hip, knee and ankle flexion that takes place during the swing phase of walking, in accordance with the principles of the present invention.
Figure 2:
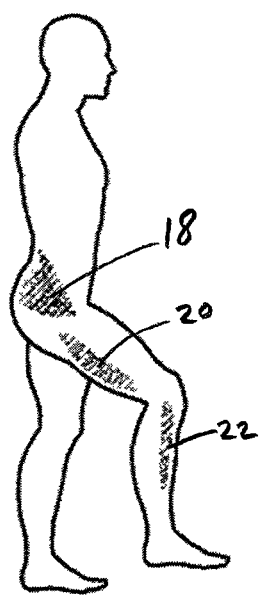
FIG. 2 is a schematic drawing of a human being illustrating the muscles involved in triple flexion of the hip flexors (illiopsoas, illiacus), the knee flexors (hamstrings) and the ankle flexors (dorsiflexors), in accordance with the principles of the present invention.
Figure 3:
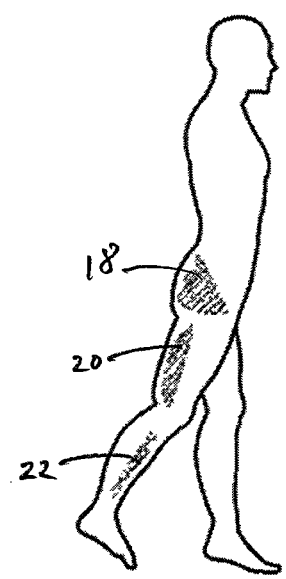
FIG. 3 is a schematic drawing of a human being having hip, knee and foot drop which occurs when the muscles responsible for flexing these joints are unable to do so due to paralysis, in accordance with the principles of the present invention.

Referring now to FIG. 1, the triple flexion device 10 of the present invention is an alternative to traditional orthotics for correcting foot drop, but in addition, it corrects hip and knee drop. In an embodiment of the present invention, the triple flexion device 10 is a light-weight and flexible device worn on the leg to provide hip, knee and ankle flexion in the swing phase of walking in people who have paralysis or are too weak to pick up their leg.

Figure 4:
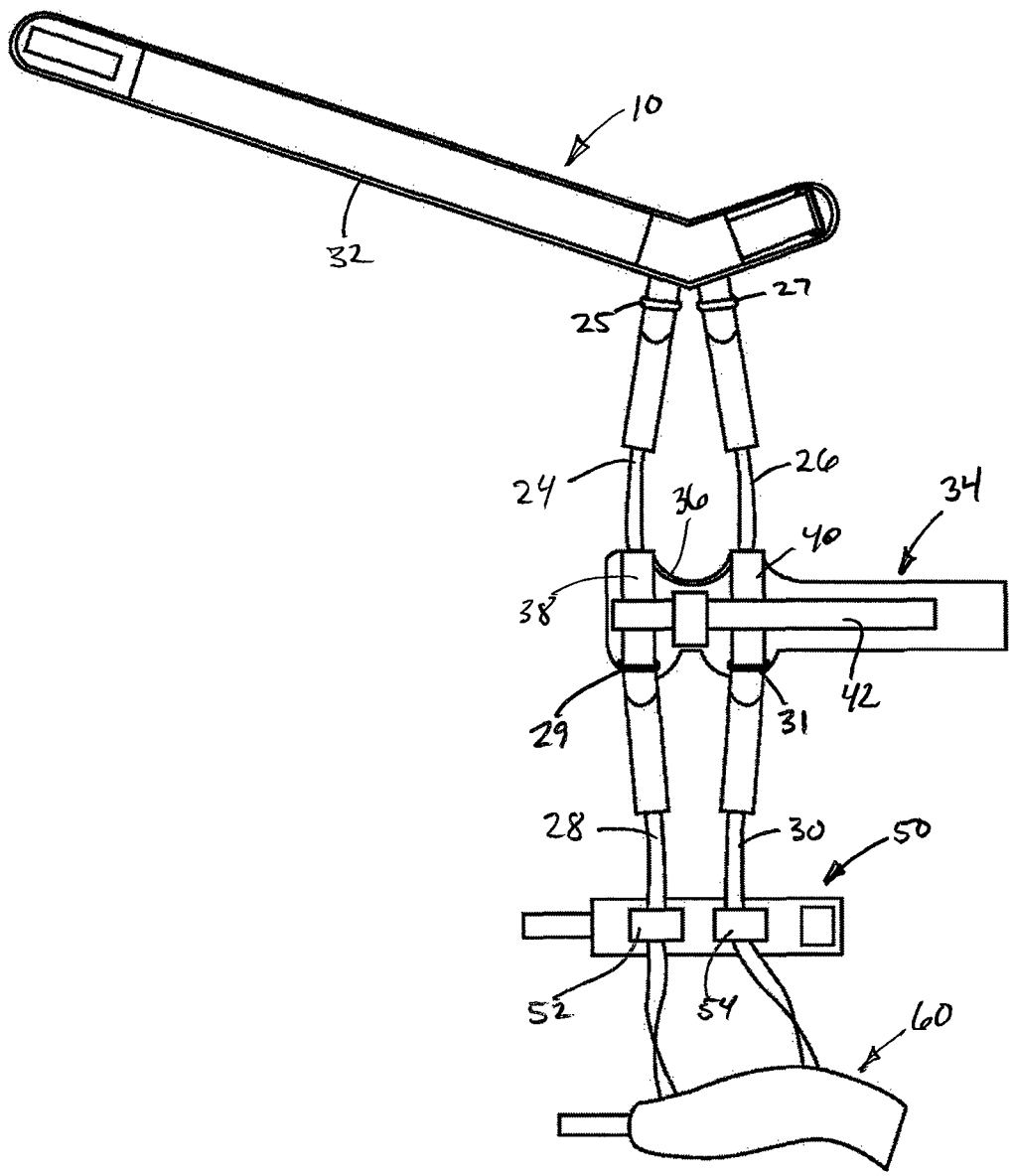
FIG. 4 is a perspective view of a triple flexion device that may be worn by a user having muscle paralysis that causes foot drop or other issues, in accordance with the principles of the present invention.
Figure 5:
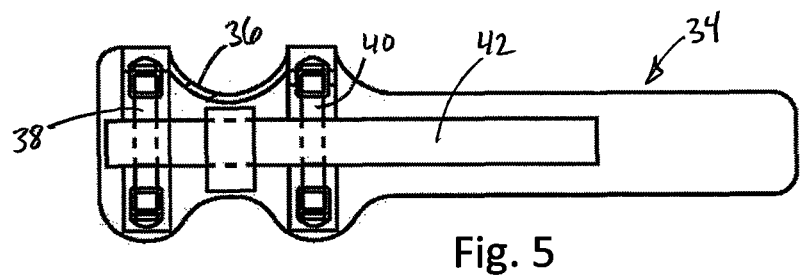
FIG. 5 is a perspective view of a knee cuff of the triple flexion device that may be worn by a user having muscle paralysis that causes foot drop or other issues, in accordance with the principles of the present invention.

Referring now to FIGS. 4 and 5, the device 10 is made of conforming material that fastens to the limb through hook and loop fastener. Accordingly, the device 10 is adjustable in size to fit a variety of people having the foot drop condition. The device 10 includes four high tension, flat elastic bands 24, 26, 28 and 30. Bands 24 and 26 are between the thigh and knee and act to flex the hip and knee. Bands 28 and 30 are between the knee and foot and act to dorsiflex the foot.

Additionally, a waist belt 32 shaped in a V is provided. The V shape of the waist belt 32 allows the waist belt to lay flat against the body as downward tension is created on waist belt 32 at the V from the two thigh elastic straps or bands 24 and 26 connected thereto. Soft padding on the underside of the waist belt 32 cushions the waist belt 32 against the skin. The waist belt 32 is retained on the pelvis though a hook and loop fastener or other fastener means and does not apply force to the lower back.

Bands 24 and 26 are adjustable by threading the bands through a pair of loops 25 and 27 that are attached to the belt 32. The bands 24, 26 are threaded through the loops and then folded back on themselves and secured through hook and loop fastening means. Similarly, bands 28 and 30 are adjustable by threading the bands through a pair of loops 29 and 31 that are attached to the knee cuff 34. The bands 28, 30 are threaded through the loops and then fold back on themselves and are secured through hook and loop fastening means.

Further, a proximal lower leg wrap-around knee cuff 34 with a cutout 36 for the patella grips the proximal lower leg to prevent rotation and distal or proximal migration of the knee cuff 34. The cutout 36 has a padded and rolled edge to increase comfort of the user and prevent skin abrasions proximate the knee. Lower leg wrap-around knee cuff 34 is connected at one end to straps 24 and 26 and at another end to straps 28 and 30. The proximal lower leg knee cuff 34 has stiffening elements 38, 40 and 42 that prevent stretch in the cuff 34 are made of Dacron or similar non-stretch, stiffening material. The anterior-proximal and the posterior-distal stiffening elements 38, 40 together prevent proximal and distal migration of the cuff 32. Preventing stretch of the cuff 34 material is critical since the cuff 34 must not migrate from its position to maintain tension in the thigh straps or bands 24 and 26 and the lower leg elastic straps or bands 28 and 30. Lower leg wrap-around knee cuff 34 is secured to the knee by a hook and loop fastener or other fastener means.

Moreover, an ankle wrap 50 is provided that has two loops 52 and 54 that allow the passage of the lower leg tension straps or bands 28 and 30, but holds the straps to the ankle wrap 50 and prevents the straps from bowstringing. Ankle wrap 50 is secured to the ankle by a hook and loop fastener or other fastener means.

Moreover, the device 10 further includes a foot wrap 60 that is connected to the straps or bands 28 and 30 and is configured to wrap around and be secured to the foot. Foot wrap 60 is secured to the foot by a hook and loop fastener or other fastener means.

Once attached to a user, as shown in FIGS. 6 and 7, device 10 operates to provide the following functions:
1) Flexes the hip in the swing phase of gait;
2) Flexes the knee in the swing phase of gait;
3) Dorsiflexes the ankle/foot in the swing phase of gait;
4) Reduces genu recurvatum (hyperextension of the knee);
5) Slows down and dampens the plantarflexion moment of the ankle at heel strike;
6) By flexing the hip, knee and ankle in the swing phase of gait, the device lowers the energy expenditure of the user who otherwise compensates for the lack of joint movements;
7) Lowers the energy and force required by the hip, knee and ankle flexors in a user who has partial paralysis and muscle weakness; and
8) When the user sits, the tension from the thigh and lower leg tension straps is eliminated so that the user sits in comfort with no forces applied to the leg.

With reference to FIGS. 8, 9 and 10, the operation of device 10 is illustrated. The lower leg elastic tension straps or bands 28 and 30 allow the foot to plantarflex. When the calf muscle relaxes, the elastic tension straps or bands 28, 30 flex the foot and ankle to 90 degrees or to a more acute angle, as shown in FIG. 9. Device 10 flexes the hip, knee and ankle which lifts the foot from the ground for much needed ground clearance during walking, as shown in FIG. 10.

Figure 11:
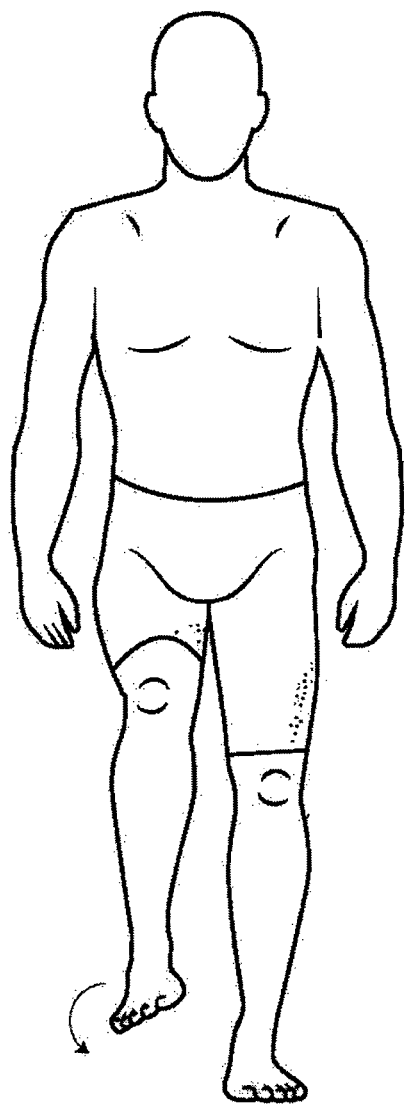
FIG. 11 is a schematic drawing of a front view of a human being demonstrating foot inversion and supination, in accordance with the principles of the present invention.
Figure 12:
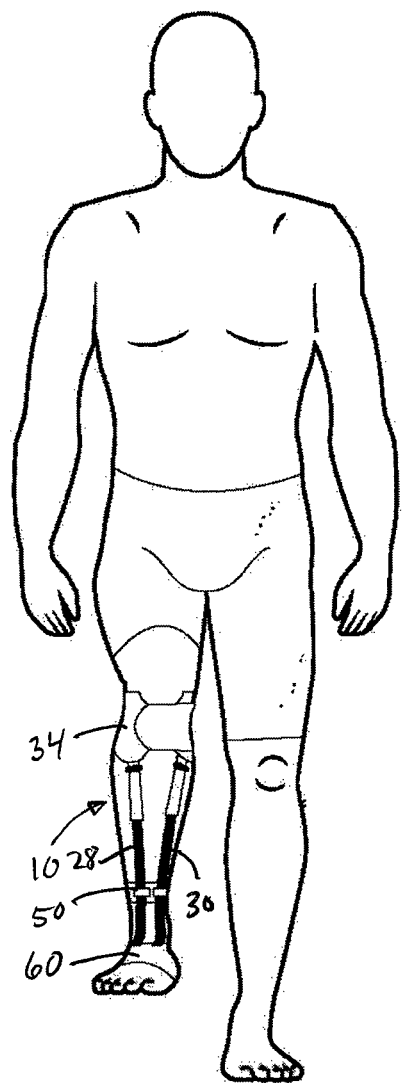
FIG. 12 is a schematic drawing of a front view of a human being wearing the triple flexion device configured to correct foot inversion and supination, in accordance with the principles of the present invention.

With reference to FIGS. 11 and 12, a user having muscle paralysis is shown without and with the device 10. Some users with paralysis of the lower leg muscles may experience not only foot drop, but a drop of the lateral aspect of the foot, also called inversion and supination, as illustrated in FIG. 11. The two elastic tension straps or bands 28, 30 attached to the foot wrap 60 are independently adjustable. The independent adjustability of the bands 28, 30 allows the user to increase the tension in the straps or bands 28, 30 which corrects inversion of the foot, as illustrated in FIG. 12. For example, the lateral elastic strap or band 28 is adjusted to increase the force on the lateral aspect of the foot.

Figure 13:
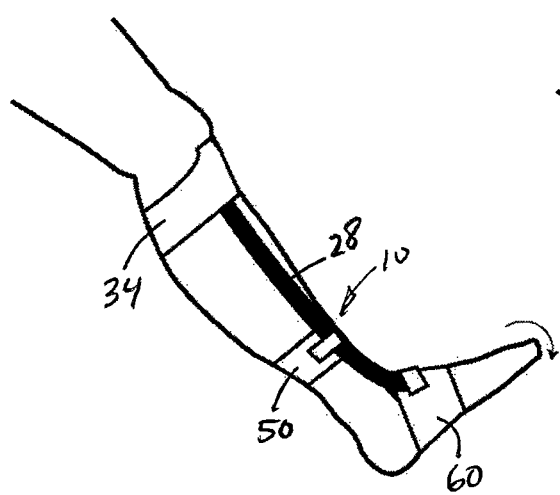
FIG. 13 is a schematic drawing of a leg of a human being wearing the triple flexion device configured to allow the foot to plantarflex, in accordance with the principles of the present invention.
Figure 14:
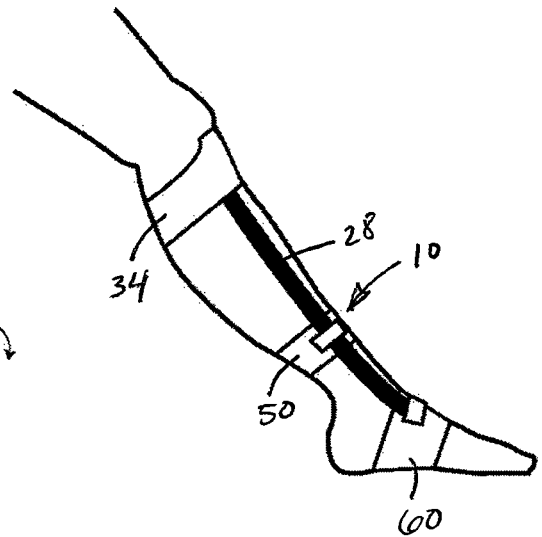
FIG. 14 is a schematic drawing of a leg of a human being wearing the triple flexion device demonstrating plantarflexing of the foot, in accordance with the principles of the present invention.

With reference to FIGS. 13 and 14, how device 10 is attached to a user and allows the user's foot to plantarflex is illustrated. The lower leg elastic tension straps or bands 28, 30 allow the foot to plantarflex when the heel strikes the ground. Advantageously, device 10 allows the foot to reach the ground until it is flat on the ground. The dampening effect of the elastic straps or bands 28, 30 prevents the foot from plantarflexing too rapidly. When the foot drops to the ground unassisted by muscles or mechanical restriction, the condition is known as foot slap. Device 10 prevents foot slap by dampening the rotation of the foot.

Figure 15:
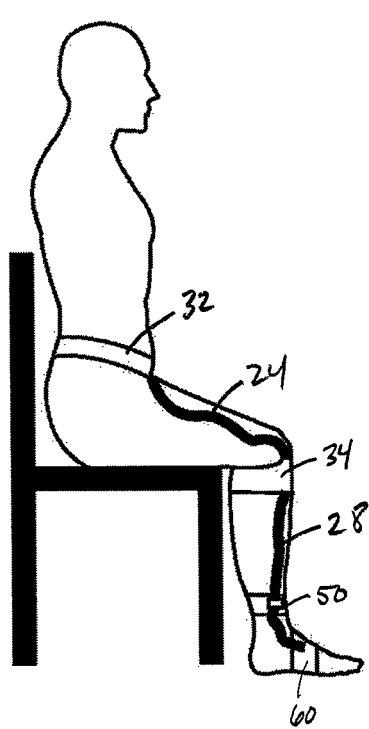
FIG. 15 is a schematic drawing of a side view of a human being seated in a chair wearing the triple flexion device configured to allow the user to sit comfortably, in accordance with the principles of the present invention.
Figure 16:
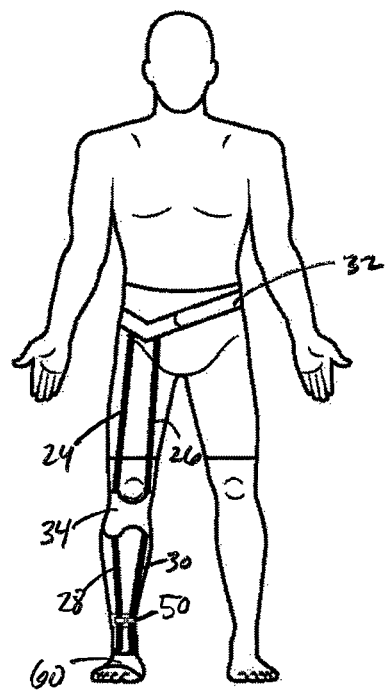
FIG. 16 is a schematic drawing of a front view of a human being standing and wearing the triple flexion device where the bands are taut, in accordance with the principles of the present invention.

With reference to FIGS. 15 and 16, device 10 attached to a user who is seated and standing is illustrated. When the user sits, the elastic tension straps or bands 28, 30 of device 10 loosen so that the user sits comfortably. When the user stands, the tension straps become taut.

Figures 17, 18:
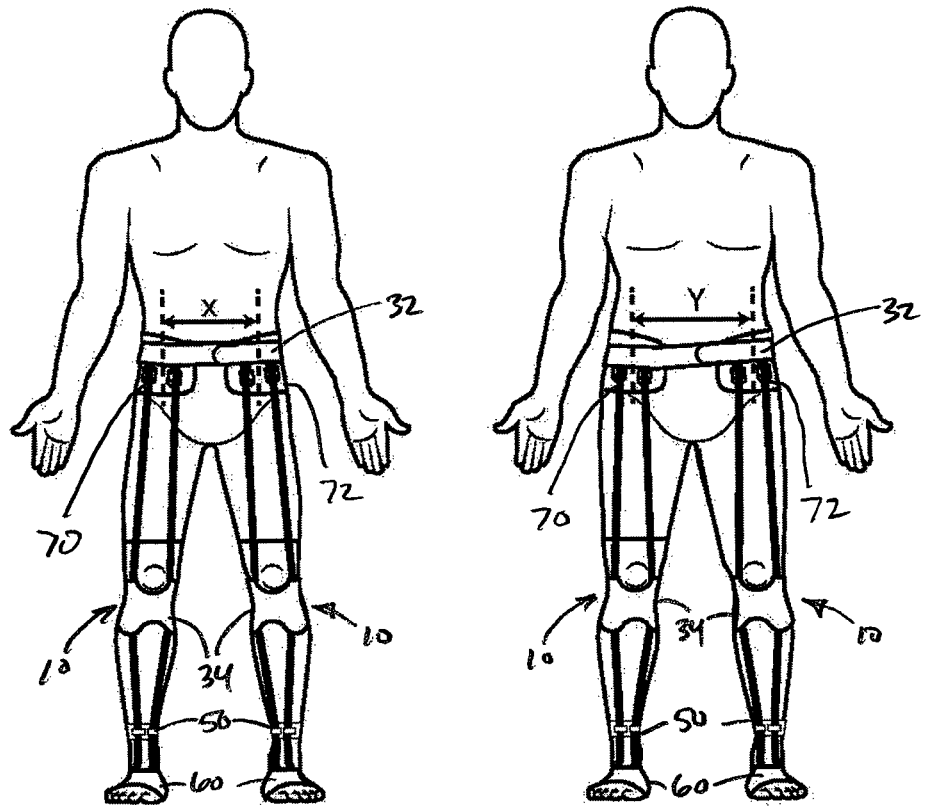
FIG. 17 is a schematic drawing of a front view of a human being wearing the triple flexion device configured to fit a user having a hip center distance of X, in accordance with the principles of the present invention.
FIG. 18 is a schematic drawing of a front view of a human being wearing the triple flexion device configured to fit a user having a hip center distance of Y, in accordance with the principles of the present invention.

With reference to FIGS. 17 and 18, device 10 attached to users of different size having different hip centers is illustrated. In another embodiment of the present invention, adjustable belt panels 70 and 72 are slidably attached to the belt 32. Adjustable belt panels 70 and 72 can adjusted by sliding the panels along the belt 32 and fixing the panels by hook and loop fastening or by other fastening means to accommodate the differences in distance between hip centers. For example, the belt panels 70 and 72 can be adjusted to accommodate a user have a hip center distance of X and belt panels 70 and 72 may be adjusted again to accommodate a user having a hip center distance of Y, where Y>X.

Figures 19, 20:
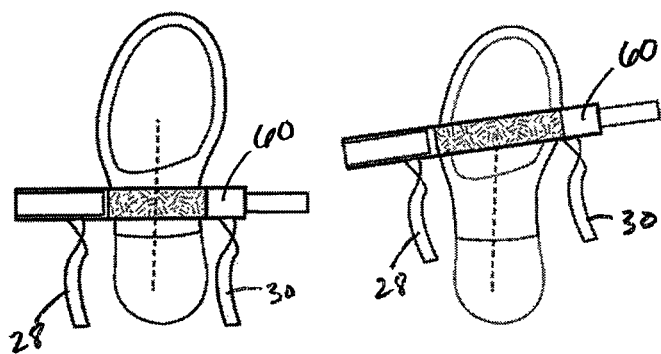
FIG. 19 is a schematic drawing of a bottom view of a shoe having the foot wrap of the triple flexion device positioned in the ach area of the shoe, in accordance with the principles of the present invention.
FIG. 20 is a schematic drawing of a bottom view of a shoe having the foot wrap of the triple flexion device positioned under the metatarsal heads of the foot, in accordance with the principles of the present invention.

With reference to FIGS. 19 and 20, two different positions or placements of the foot wrap or shoe strap 60 of device 10 are illustrated. The foot wrap or shoe strap 60 can be positioned in the arch area of the shoe or underneath the metatarsal heads of the foot. The advantage of placing the foot wrap or shoe strap 60 under the metatarsal heads is to increase the lifting force of the foot.

Figure 21:
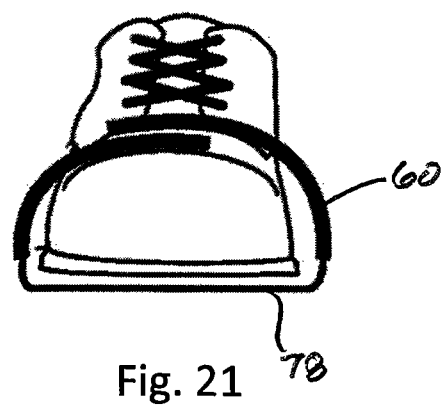
FIG. 21 is a schematic drawing of a front view of a shoe having the foot wrap of the triple flexion device positioned under the shoe, in accordance with the principles of the present invention.

FIG. 21 illustrates a soling material of foot wrap or shoe strap 60 of device 10 wrapping around the plantar surface of the shoe. Foot wrap or shoe strap 60 of device 10 includes soling material 78 that wraps around the sole of the shoe on the inside and outside of the shoe. The foot wrap 60 closes with a hook and loop fastener or similar fastening system. The soling material 78 is thin, yet durable enough to withstand the wear and tear of normal walking.

Figure 22:
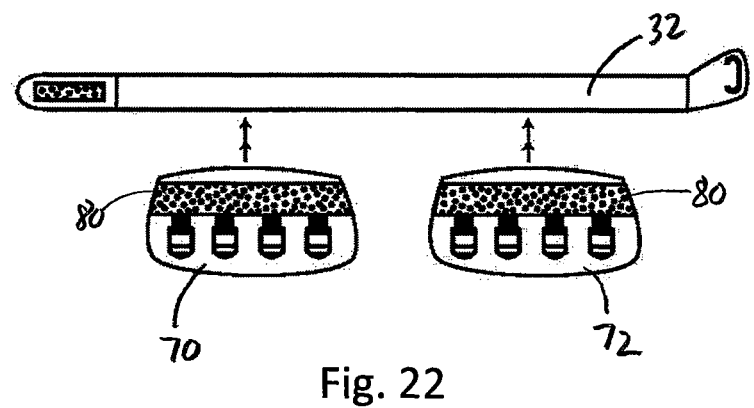
FIG. 22 is a schematic drawing of the belt and adjustable panels of the triple flexion device where the panels are detached from the belt, in accordance with the principles of the present invention.
Figure 23:
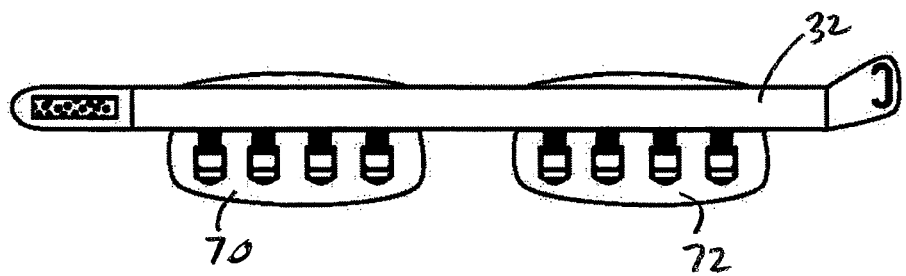
FIG. 23 is a schematic drawing of the belt and adjustable panels of the triple flexion device where the panels are attached to the belt, in accordance with the principles of the present invention.

With reference to FIGS. 22 and 23, the adjustability of the panels 70 and 72 on the belt 32 is illustrated. Advantageously, the modularity of the device 10 and the waist belt 32 with panels 70 and 72 is shown. The panels are connected to the belt 32 with hook and loop fastener system 80 or similar fastening means and, thus, the panels 70 and 72 may be positioned anywhere along the belt 32. The hook part of the hook and loop fastener system 80 is attached to the panels 70 and 72 while the loop part of the hook and loop fastener system 80 is attached to the underside of the belt 32. Of course, the present invention contemplates that alternatively the loop part of the hook and loop fastener system 80 is attached to the panels 70 and 72 while the hook part of the hook and loop fastener system 80 is attached to the underside of the belt 32.

With reference to FIG. 24, a cross-section through a user's torso at the hips is illustrated showing the hip centers 82, 84 and the adjustability of the panels 70 and 72 on the belt 32 relative to the hip centers. As shown, panels 70 and 72 may be adjusted or shifted along the belt 32 of device 10 to different positions in relation to the left and right hip centers 82, 84 to address different user issues. Depending on where the panels 70 and 72 are placed with respect to a hip center 82, 84, device 10 will impart various movements to the lower extremity.

Figure 31:
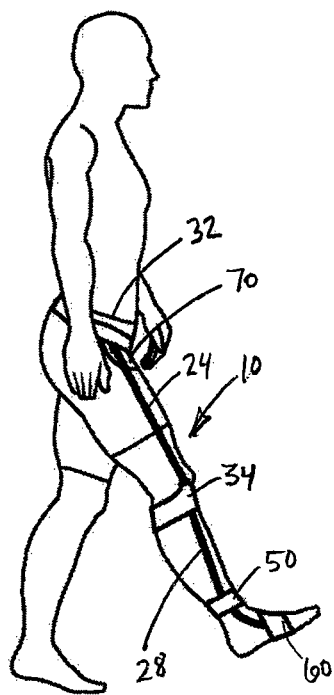
FIG. 31 is a schematic drawing of a side view of a human being wearing the triple flexion device configured to move the leg forward, in accordance with the principles of the present invention.
Figure 32:
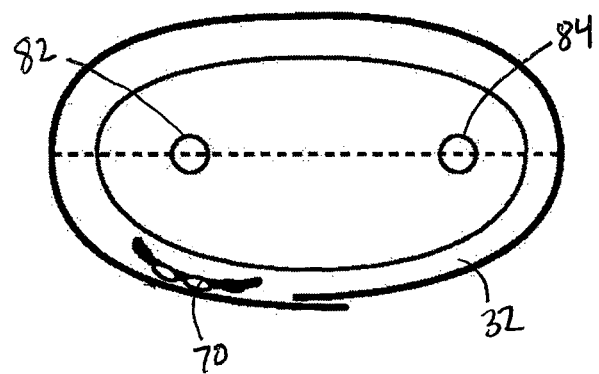
FIG. 32 is a schematic drawing of a cross-section of a human being at the hip centers wearing the triple flexion device and illustrating the location of the adjustable panel on the belt to move the leg forward, in accordance with the principles of the present invention.

For example as shown in FIGS. 25 and 26, when the adjustable panel is placed lateral to the hip center 82 with the active straps or bands 24, 26 located laterally, device 10 will abduct the hip. It should be noted, that the locations of the active straps or bands 24, 26 are equally spaced anterior and posterior to the hip center line. Thus, equal force on the hip is created that abducts the hip without deviation anteriorly or posteriorly. Combined movements can be created by choosing active strap or bands 24, 26 locations that produce the desired movement. Moreover, FIGS. 27 and 28 illustrate the position of the adjustable panels 70 or 72 required to adduct the right hip. As shown, the panel 72 is positioned proximate the left hip center 84. Accordingly, FIGS. 29 and 30 illustrate the position of the adjustable panel 70 required to rotate the right hip. As shown, the panel 70 is positioned proximate the right hip center 82 and towards the side of the user. Further, FIGS. 31 and 32 illustrate the position of the adjustable panel 70 required to move the right leg forward. As shown, the panel 70 is positioned proximate the right hip center 82 and towards the front of the user.

Figure 33:
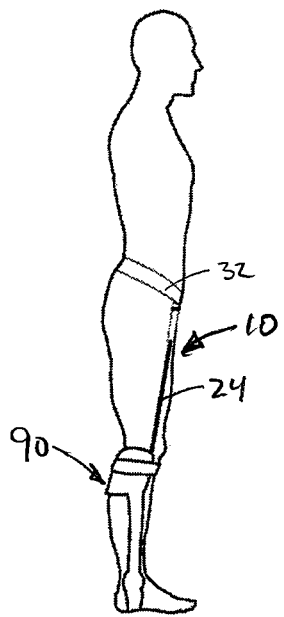
FIG. 33 is a schematic drawing of a side view of a human being wearing the triple flexion device in combination with an Ankle Foot Orthosis, in accordance with the principles of the present invention.

Referring now to FIGS. 33, 34 and 35, a perspective view of a user wearing the device 10 in conjunction with other devices to treat muscular deficiencies and other problems are illustrated. For example, device 10 may be configured to be worn with an Ankle Foot Orthosis (AFO) 90, as shown in FIG. 33. Alternatively, device 10 may be configured to be worn with a Functional Electrical Stimulation (FES) device 92, as shown in FIG. 34. In yet another embodiment of the present invention, device 10 may be configured to be worn with a Knee Orthosis 94, as shown in FIG. 35.

The present invention has many advantages and benefits over the prior are the following are just a few: 1) Adjustable tension elastic straps or bands 24, 26, 28 and 30 that flex the hip and knee. 2) Adjustable tension elastic straps or bands 24, 26, 28 and 30 that dorsiflex the foot. 3) Waist belt 32 shaped in a V allows the waist belt to lay flat against the body as downward tension is created on waist belt 32 at the V from the two thigh elastic straps or bands 24, 26 and soft padding on the underside of the belt cushions the waist belt 32 against the skin. The waist belt 32 is retained on the pelvis and does not apply force to the lower back. 4) Proximal lower leg wrap-around cuff 34 with cut out for the patella grips the proximal lower leg to prevent rotation and distal or proximal migration of the cuff 34. 5) The proximal lower leg cuff 34 has 38, 40 and 42 stiffening elements that prevent stretch in the cuff 34. The anterior-proximal and the posterior-distal stiffening elements together prevent proximal and distal migration of the cuff 34. Preventing stretch of the cuff 34 material is critical since the cuff 34 must not migrate from its position to maintain tension in the thigh and the lower leg elastic straps or bands 24, 26. 6) The position of the thigh and lower leg elastic straps or bands 24, 26 provide balancing forces to each other. The force generated in the thigh elastic straps or bands 24, 26 tend to draw the lower leg cuff 34 proximally while the lower leg elastic straps or bands 28, 30 tend to draw the lower leg cuff 34 distally. These opposing forces tend to help keep the cuff 34 from shifting proximally or distally. The lessening of forces on the cuff 34 makes the cuff 34 more comfortable on the user (see FIGS. 4, 5 and 6). 7) The U-shaped cut-out 36 on the lower leg cuff 34 contours around the distal aspect of the patella and is padded and more comfortable on the user. 8) The two lower leg elastic straps or bands 28, 30 provide foot dorsiflexion (see FIGS. 4, 5 and 6). When the lateral elastic strap or band 28 is adjusted with greater tension than the medial strap or band 30, the foot will invert. This is critically important in users who have foot drop resulting in an inverted foot. An inverted foot will strike the ground on the lateral border of the foot which can be painful and can cause pressure breakdown. The user can adjust the lateral strap or band 28 to apply increased tension in the strap 28 until the foot no longer inverts. To achieve neutral position of the foot in the coronal plane, the lateral tension strap or band 28 should be greater than the medial tension strap or band 30. 9) The ankle strap 50 has two loops that allow the passage of the lower leg tension straps or bands 28, 30, but holds bands 28, 30 to the ankle and prevents bands 28, 30 from bowstringing. 10) The foot wrap 60 secures the lower leg tension straps or bands 28, 30 to the foot. 11) When the user sits, the elastic straps or bands 24, 26, 28, 30 loosen so there is no tension in the straps. This makes sitting comfortable (see FIG. 15). 12) The tension straps or bands 24, 26, 28, 30 keep the foot dorsiflexed so that the heel strikes the ground first as necessary for normal walking (see FIG. 31). The lower leg elastic straps or bands 28, 30 lengthen as the heel strikes the ground. This added tension in the straps dampens the angular forces at the ankle. This softens the forces of the foot as it strikes the ground. The lengthening of the lower leg elastic straps or bands 28, 30 allow the foot to plantarflex as the foot should in normal walking.

The description of the invention is merely exemplary in nature and variations that do not depart from the gist of the invention are intended to be within the scope of the invention. Such variations are not to be regarded as a departure from the spirit and scope of the invention.

What is claimed is:

1. A device for assisting with hip, knee and ankle flexion, the device comprising:
    a belt configured to be worn around a waist of a user wherein the belt is V-shaped and the first adjustable elastic band of the first pair of elastic bands is connected to the belt at a first side of the V-shape and the second adjustable elastic band of the first pair of elastic bands is connected to the belt at a second side of the V-shape;
    a knee cuff configured to wrap around a knee of the user and positioned below the belt;
    a foot wrap configured to wrap around a foot of the user and positioned below the knee cuff;
    two pairs of adjustable elastic bands wherein the first pair each have a first end adjustably connected to the belt and a second end securely fixed to the knee cuff and wherein the second pair each have a first end adjustably connected to the knee cuff and a second end securely fixed to the foot wrap;
    an ankle wrap configured to wrap around an ankle of the user and positioned between the knee cuff and the foot wrap, wherein the ankle wrap has two loops spaced from one another, wherein each loop receives there through one of the second pair of adjustable elastic bands to space each of the second pair of adjustable elastic bands about a user's ankle;
    wherein the knee cuff includes a u-shaped cutout configured to contour around a lower aspect of a patella of the user with the u-shaped cutout opening upwards toward the waist of the user, and a first adjustable elastic band of the first pair of elastic bands is connected to the knee cuff at a first end of the u-shaped cutout and extends toward and connects to the belt and a second adjustable elastic band of the first pair of elastic bands is connected to the knee cuff at a second end of the u-shaped cutout and extends toward and connects to the belt;
    wherein the belt is V-shaped and the first adjustable elastic band of the first pair of elastic bands is connected to the belt at a first side of the V-shape and the second adjustable elastic band of the first pair of elastic bands is connected to the belt at a second side of the V-shape; and
    whereby, triple flexion occurs in the hip, knee and ankle of the user during a swing phase of walking when the user has the belt wrapped around the user's waist, the knee cuff wrapped around the user's knee, the ankle wrap wrapped around the user's ankle, and the foot and the foot wrap wrapped around the user's foot.

2. The device of claim 1, wherein the belt is fastened to the user's waist using a hook and loop fastener.

3. The device of claim 2, wherein the belt has a padded underside.

4. The device of claim 1, wherein the knee cuff has a plurality of stiffening members.

5. The device of claim 4, wherein the knee cuff has a hook and loop fastener to fasten the knee cuff around the user's knee.

6. The device of claim 1, wherein the ankle wrap has a hook and loop fastener to fasten the ankle wrap around the user's ankle.

7. The device of claim 1, wherein the foot wrap has a hook and loop fastener to fasten the foot wrap around the user's foot.

* * * * *